US010219991B2

(12) United States Patent
Daubersies et al.

(10) Patent No.: US 10,219,991 B2
(45) Date of Patent: Mar. 5, 2019

(54) COMPOSITION COMPRISING POLYMER PARTICLES, A HYDROCARBON-BASED OIL AND A SILICONE RESIN, AND PROCESS USING THE SAME

(71) Applicant: L'OREAL, Paris (FR)

(72) Inventors: Laure Daubersies, Paris (FR); Nathalie Gavache, Orleans (FR); Stephane Douezan, Le Kremlin Bicetre (FR)

(73) Assignee: L'OREAL, Paris (FR)

( * ) Notice: Subject to any disclaimer, the term of this patent is extended or adjusted under 35 U.S.C. 154(b) by 58 days.

(21) Appl. No.: 15/537,082

(22) PCT Filed: Dec. 11, 2015

(86) PCT No.: PCT/EP2015/079341
§ 371 (c)(1),
(2) Date: Jun. 16, 2017

(87) PCT Pub. No.: WO2016/096627
PCT Pub. Date: Jun. 23, 2016

(65) Prior Publication Data
US 2017/0360684 A1 Dec. 21, 2017

(30) Foreign Application Priority Data
Dec. 18, 2014 (FR) ...................................... 14 62744

(51) Int. Cl.
A61K 8/02 (2006.01)
A61K 8/81 (2006.01)
A61K 8/31 (2006.01)
A61Q 1/10 (2006.01)
A61K 8/891 (2006.01)
C08F 265/06 (2006.01)
C08L 33/08 (2006.01)
C08L 51/00 (2006.01)
A61K 8/04 (2006.01)
C08F 220/14 (2006.01)

(52) U.S. Cl.
CPC .......... A61K 8/8152 (2013.01); A61K 8/0241 (2013.01); A61K 8/04 (2013.01); A61K 8/31 (2013.01); A61K 8/8164 (2013.01); A61K 8/891 (2013.01); A61Q 1/10 (2013.01); C08F 220/14 (2013.01); C08F 265/06 (2013.01); C08L 33/08 (2013.01); C08L 51/00 (2013.01); A61K 2800/52 (2013.01); A61K 2800/594 (2013.01); A61K 2800/614 (2013.01); A61K 2800/654 (2013.01); C08L 2205/02 (2013.01)

(58) Field of Classification Search
None
See application file for complete search history.

(56) References Cited

U.S. PATENT DOCUMENTS

| 5,616,598 A | 4/1997 | Lion et al. |
| 5,851,517 A | 12/1998 | Mougin et al. |
| 5,945,095 A | 8/1999 | Mougin et al. |
| 2004/0137028 A1 | 7/2004 | de la Poterie |
| 2009/0196839 A1 | 8/2009 | Farcet et al. |
| 2011/0243864 A1 | 10/2011 | Farcet et al. |
| 2011/0268675 A1 | 11/2011 | Ureneck et al. |

FOREIGN PATENT DOCUMENTS

| EP | 0 749 746 | 12/1996 |
| EP | 0 749 747 | 12/1996 |
| FR | 2 785 530 | 5/2000 |
| FR | 2 880 267 A1 | 7/2006 |
| FR | 2 927 082 A1 | 8/2009 |
| FR | 2 937 645 | 4/2010 |
| FR | 2 972 630 A1 | 9/2012 |
| FR | 2 972 631 A1 | 9/2012 |
| WO | WO 2005/060922 A1 | 7/2005 |
| WO | WO 2010/088212 A1 | 8/2010 |

OTHER PUBLICATIONS

U.S. Appl. No. 14/575,259, filed Dec. 18, 2014, 2016/0175204, Rita Jaky El-Khouri.
U.S. Appl. No. 14/575,419, filed Dec. 18, 2014, 2016/0175230, Susan Halpern-Chirch.
U.S. Appl. No. 14/575,866, filed Dec. 18, 2014, US2016/0175232, Rita Jaky El-Khouri.
U.S. Appl. No. 14/974,531, filed Dec. 18, 2015, 2016/0184211, Roshanak Debeaud.
U.S. Appl. No. 14/974,706, filed Dec. 18, 2015, 2016/0175205, Roshanak Debeaud.
U.S. Appl. No. 15/105,293, filed Jun. 16, 2016, 2016/0317423, Julien Portal.
U.S. Appl. No. 15/533,444, filed Jun. 6, 2017, Hong Li.
U.S. Appl. No. 15/534,216, filed Jun. 8, 2017, Roshanak Debeaud.

(Continued)

Primary Examiner — Nannette Holloman
(74) Attorney, Agent, or Firm — Oblon, McClelland, Maier & Neustadt, L.L.P.

(57) ABSTRACT

The present invention relates to a composition comprising particles of at least one polymer that is surface-stabilized with a stabilizer, the polymer of the particles being a C1-C4 alkyl (meth)acrylate polymer; the stabilizer being an isobornyl (meth)acrylate polymer chosen from isobornyl (meth)acrylate homopolymer and statistical copolymers of isobornyl (meth)acrylate and of C1-C4 alkyl (meth)acrylate present in an isobornyl (meth)acrylate/C1-C4 alkyl (meth)acrylate weight ratio of greater than 4, at least one hydrocarbon-based oil and at least one silicone resin, and a mixture thereof. The invention also relates to a process for making up and/or caring for keratin materials, in which said composition is applied.

19 Claims, No Drawings

(56) References Cited

OTHER PUBLICATIONS

U.S. Appl. No. 15/537,422, Philippe Ilekti.
U.S. Appl. No. 15/537,423, Philippe Ilekti.
U.S. Appl. No. 15/535,963, filed Jun. 14, 2017, Laure Daubersies.
International Search Report dated Feb. 3, 2016, in PCT/EP2015/079341 filed Dec. 11, 2015.

COMPOSITION COMPRISING POLYMER PARTICLES, A HYDROCARBON-BASED OIL AND A SILICONE RESIN, AND PROCESS USING THE SAME

CROSS REFERENCE TO RELATED APPLICATIONS

This application is the National Stage of PCT/EP2015/079341, filed Dec. 11, 2015, the disclosure of which is incorporated herein by reference in its entirety. PCT/EP2015/079341 claims priority to French Application No. 1462744, filed Dec. 18, 2014, the disclosure of which is incorporated herein by reference in its entirety.

BACKGROUND

The present invention relates to compositions for making up and/or caring for human keratin materials, such as the skin, the lips and keratin fibres especially such as the eyelashes or the eyebrows, comprising polymer particles, at least one hydrocarbon-based oil and at least one silicone resin.

The invention similarly relates to a process for making up and/or caring for human keratin materials, for instance the skin and the lips, but also keratin fibres especially such as the eyelashes and the eyebrows, which consists in applying the composition according to the invention.

It has been sought in recent years to obtain compositions whose deposit is persistent and glossy. The persistence of the deposit avoids, on the one hand, the need to reapply the composition too often and, on the other hand, reduces transfer of the composition onto supports with which the made-up areas come into contact (clothing, cups, etc.) or else their removal via the action of external agents (sebum, food, rain, etc.).

This result is achieved by using a film-forming agent, which is often a polymer in a solubilized form or dispersed in one of the phases of the composition. Said agent allows the composition, once applied, to form after drying a film that is more cohesive and persistent on the support.

One of the problems encountered with such film-forming agents lies in the fact that the compositions containing them give a deposit which, once dry, appreciably loses its gloss. Now, this may be perceived as a drawback in the case of certain applications in which not only persistence but also gloss are desired.

The use of very glossy film-forming agents, such as those used in nail varnish compositions, is clearly unsuitable for compositions for making up the skin, the eyelashes or the eyebrows, for example. Specifically, the film obtained would be considered as being too rigid for this type of support, and thus uncomfortable. In addition, the deposit would run the risk of being brittle, which might lead to crumbling of the composition once it is dried.

As an alternative to this problem, it has been proposed to use "two-action" compositions, i.e. compositions which require the implementation of two steps, the first consisting in applying the composition containing the film-forming polymer and ensuring good persistence, and the second providing the gloss. These processes represent an improvement in terms of gloss of the deposit, but they are more complicated than standard one-step processes. They also cannot be transposed to all makeup compositions.

Another envisaged route is to add to the composition at least one glossy non-volatile oil. In this case also, this process cannot be used for all types of makeup compositions, in particular those for which the deposit is expected to dry relatively rapidly, to limit the sensation of tack during this period, and also the risks of running of the composition beyond the made-up area.

SUMMARY OF THE INVENTION

The present invention thus relates to compositions for making up and/or caring for human keratin materials, for which it is especially sought to obtain glossy and persistent films.

One subject of the invention is thus a composition comprising particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, at least one hydrocarbon-based oil and at least one silicone resin.

A subject of the invention is also a process for making up and/or caring for keratin materials, in particular the skin, the lips and keratin fibres such as the eyelashes and the eyebrows, which consists in applying said composition.

DESCRIPTION OF THE PREFERRED EMBODIMENTS

It has thus been found that the composition according to the invention makes it possible to obtain glossy, non-tacky, comfortable films that have good persistence and are transfer-resistant.

Moreover, and this represents another advantage of the composition according to the invention, it is easy and quick to apply.

In addition, the tack peak that is often encountered during the application of these makeup compositions, is not pronounced and does not interfere with their application.

However, other advantages will emerge more clearly on reading the description and the examples that follow.

It should be noted that, in the remainder of the description, unless otherwise indicated, the limits indicated for a range are included in that range.

The expressions "at least one" and "several" are used without distinction.

Hydrocarbon-Based Oil

The composition according to the invention comprises a hydrocarbon-based oil.

This oil may be volatile (vapour pressure greater than or equal to 0.13 Pa measured at 25° C.) or non-volatile (vapour pressure less than 0.13 Pa measured at 25° C.).

Preferably, the hydrocarbon-based oil is volatile.

The hydrocarbon-based oil is an oil (non-aqueous compound) that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be chosen from:
  hydrocarbon-based oils containing from 8 to 16 carbon atoms, and especially:
    branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade name Isopar or Permethyl, linear alkanes, for instance n-dodecane ($C_{12}$) and n-tetradecane ($C_{14}$) sold by Sasol under the respective references Parafol 12-97 and Parafol 14-97, and also mixtures thereof, the undecane-tridecane mixture, the mixtures of n-undecane ($C_{11}$) and of n-tridecane ($C_{13}$) obtained in Examples 1 and 2 of patent application WO 2008/155 059 from the company Cognis, and mixtures thereof, short-chain esters (containing from 3 to 8 carbon atoms in total) such as ethyl acetate, methyl acetate, propyl acetate or n-butyl acetate, hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stearineries Dubois or those sold under the names Miglyol 810®, 812° and 818° by the company Dynamit Nobel, synthetic ethers containing from 10 to 40 carbon atoms, linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula $R_1COOR_2$ in which $R_1$ represents a linear or branched fatty acid residue containing from 1 to 40 carbon atoms and $R_2$ represents an in particular branched hydrocarbon-based chain containing from 1 to 40 carbon atoms, on the condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol, a mixture thereof.

More particularly, the content of hydrocarbon-based oil(s) ranges from 20% to 75% by weight, more particularly from 30% to 75% by weight and preferably from 40% to 60% by weight, relative to the weight of the composition.

This hydrocarbon-based oil may be provided totally or partly with the surface-stabilized polymer particles, in particular when these particles are introduced into the composition in the form of a pre-prepared dispersion of stabilized polymer particles. In this case, the hydrocarbon-based oil present in the composition represents at least the non-aqueous medium of the dispersion of polymer particles.

Advantageously, the hydrocarbon-based oil is apolar (thus formed solely from carbon and hydrogen atoms).

The hydrocarbon-based oil is preferably chosen from hydrocarbon-based oils containing from 8 to 16 carbon atoms and better still from 12 to 16 carbon atoms, in particular the apolar oils described previously.

Preferentially, the hydrocarbon-based oil is isododecane. More particularly, the isododecane content ranges from 20% to 75% by weight, more particularly from 30% to 75% by weight and preferably from 40% to 60% by weight, relative to the weight of the composition.

Preferably, the hydrocarbon-based oil(s), in particular isododecane, constitute the only oil(s) of the composition, or are present in a predominant weight content relative to the additional oil(s) that may be present in the composition.

In accordance with a particular embodiment of the invention, if the composition contains one or more non-volatile oils, their content advantageously does not exceed 20% by weight, preferably does not exceed 10% by weight, preferably does not exceed 5% by weight relative to the weight of the composition, and better still does not exceed 2% by weight relative to the weight of the composition, or even is free of non-volatile oil(s).

Polymer Particles

The composition according to the invention moreover comprises particles, which are generally spherical, of at least one surface-stabilized polymer.

Preferably, the particles are introduced into the composition in the form of a dispersion of particles, which are generally spherical, of at least one surface-stabilized polymer, in an oily (non-aqueous) medium, advantageously containing at least one hydrocarbon-based oil, as defined previously.

The polymer of the particles is a $C_1$-$C_4$ alkyl (meth) acrylate polymer.

The $C_1$-$C_4$ alkyl (meth)acrylate monomers may be chosen from methyl (meth)acrylate, ethyl (meth)acrylate, n-propyl (meth)acrylate, isopropyl (meth)acrylate, n-butyl (meth) acrylate and tert-butyl (meth)acrylate.

A $C_1$-$C_4$ alkyl acrylate monomer is advantageously used. Preferentially, the polymer of the particles is a methyl acrylate and/or ethyl acrylate polymer.

The polymer of the particles may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof.

Preferably, the ethylenically unsaturated acid monomer is chosen from (meth)acrylic acid, maleic acid and maleic anhydride.

The salts may be chosen from salts of alkali metals, for example sodium or potassium; salts of alkaline-earth metals, for example calcium, magnesium or strontium; metal salts, for example zinc, aluminium, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles may thus comprise or consist essentially of 80% to 100% by weight of $C_1$-$C_4$ alkyl (meth)acrylate and of 0 to 20% by weight of ethylenically unsaturated acid monomer, relative to the total weight of the polymer.

According to a first embodiment of the invention, the polymer consists essentially of a polymer of one or more $C_1$-$C_4$ alkyl (meth)acrylate monomers.

According to a second embodiment of the invention, the polymer consists essentially of a copolymer of $C_1$-$C_4$ (meth) acrylate and of (meth)acrylic acid or maleic anhydride.

The polymer of the particles may be chosen from:
methyl acrylate homopolymers
ethyl acrylate homopolymers
methyl acrylate/ethyl acrylate copolymers
methyl acrylate/ethyl acrylate/acrylic acid copolymers
methyl acrylate/ethyl acrylate/maleic anhydride copolymers
methyl acrylate/acrylic acid copolymers
ethyl acrylate/acrylic acid copolymers
methyl acrylate/maleic anhydride copolymers
ethyl acrylate/maleic anhydride copolymers.

Advantageously, the polymer of the particles is a non-crosslinked polymer.

The polymer of the particles preferably has a number-average molecular weight ranging from 2000 to 10 000 000 and preferably ranging from 150 000 to 500 000.

In the case of a particle dispersion, the polymer of the particles may be present in the dispersion in a content ranging from 21% to 58.5% by weight and preferably ranging from 36% to 42% by weight, relative to the total weight of the dispersion.

The stabilizer is an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth) acrylate/$C_1$-$C_4$ alkyl (meth)acrylate weight ratio of greater than 4, preferably greater than 4.5 and even more advantageously greater than or equal to 5. Advantageously, said weight ratio ranges from 4.5 to 19, preferably from 5 to 19 and more particularly from 5 to 12.

Advantageously, the stabilizer is chosen from:
isobornyl acrylate homopolymers
statistical copolymers of isobornyl acrylate/methyl acrylate
statistical copolymers of isobornyl acrylate/methyl acrylate/ethyl acrylate
statistical copolymers of isobornyl methacrylate/methyl acrylate
in the weight ratio described previously.

Preferably, the stabilizer is soluble in the hydrocarbon-based oil(s), in particular soluble in isododecane.

The stabilizing polymer preferably has a number-average molecular weight ranging from 10 000 to 400 000 and preferably ranging from 20 000 to 200 000.

The stabilizer is in contact with the surface of the polymer particles and thus makes it possible to stabilize these particles at the surface, in particular in order to keep these particles in dispersion in the non-aqueous medium of the dispersion.

According to a theory which should not limit the scope of the present invention, the inventors put forward the hypothesis that the surface stabilization of the $C_1$-$C_4$ alkyl (meth) acrylate polymer particles results from a phenomenon of surface adsorption of the stabilizer onto the $C_1$-$C_4$ alkyl (meth)acrylate polymer particles.

Advantageously, the combination of the stabilizer+polymer of the particles present in particular in the dispersion comprises from 10% to 50% by weight of polymerized isobornyl (meth)acrylate and from 50% to 90% by weight of polymerized $C_1$-$C_4$ alkyl (meth)acrylate, relative to the total weight of the combination of the stabilizer+polymer of the particles.

Preferentially, the combination of the stabilizer+polymer of the particles present in particular in the dispersion comprises from 15% to 30% by weight of polymerized isobornyl (meth)acrylate and from 70% to 85% by weight of polymerized $C_1$-$C_4$ alkyl (meth)acrylate, relative to the total weight of the combination of the stabilizer+polymer of the particles.

When the polymer particles are provided in the composition in the form of a pre-prepared dispersion, the oily medium of this polymer dispersion comprises a hydrocarbon-based oil. Reference may be made to that which has been indicated previously concerning this oil as regards its nature.

Advantageously, the hydrocarbon-based oil is apolar and preferably chosen from hydrocarbon-based oils containing from 8 to 16 carbon atoms, in particular the apolar oils described previously.

Preferentially, the hydrocarbon-based oil is isododecane.

The polymer particles, in particular in the dispersion, preferably have an average size, especially a number-average size, ranging from 50 to 500 nm, especially ranging from 75 to 400 nm and better still ranging from 100 to 250 nm.

In general, a dispersion of polymer particles that is suitable for use in the invention may be prepared in the following manner, which is given as an example.

The polymerization may be performed in dispersion, i.e. by precipitation of the polymer during formation, with protection of the formed particles with a stabilizer.

In a first step, the stabilizing polymer is prepared by mixing the constituent monomer(s) of the stabilizing polymer, with a radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with said synthesis solvent) and selectively distilling off the synthesis solvent.

A synthesis solvent which is such that the monomers of the stabilizing polymer and the free-radical initiator are soluble therein, and the polymer particles obtained are insoluble therein, so that they precipitate therein during their formation, is thus chosen.

In particular, the synthesis solvent may be chosen from alkanes such as heptane or cyclohexane.

When the non-aqueous medium is a volatile hydrocarbon-based oil, the polymerization may be performed directly in said oil, which thus also acts as synthesis solvent. The monomers should also be soluble therein, as should the free-radical initiator, and the polymer of the particles obtained should be insoluble therein.

The monomers are preferably present in the synthesis solvent, before polymerization, in a proportion of 5-20% by weight. The total amount of monomers may be present in the solvent before the start of the reaction, or part of the monomers may be added gradually as the polymerization reaction proceeds.

The free-radical initiator may especially be azobisisobutyronitrile or tert-butyl peroxy-2-ethylhexanoate.

The polymerization may be performed at a temperature ranging from 70 to 110° C.

The polymer particles are surface-stabilized, when they are formed during the polymerization, by means of the stabilizer.

The stabilization may be performed by any known means, and in particular by direct addition of the stabilizer, during the polymerization.

The stabilizer is preferably also present in the mixture before polymerization of the monomers of the polymer of the particles. However, it is also possible to add it continuously, especially when the monomers of the polymer of the particles are also added continuously.

From 10% to 30% by weight and preferably from 15% to 25% by weight of stabilizer may be used relative to the total weight of monomers used (stabilizer+polymer of the particles).

The polymer particle dispersion advantageously comprises from 30% to 65% by weight and preferably from 40% to 60% by weight of solids, relative to the total weight of the dispersion.

Moreover, the composition according to the invention advantageously comprises a content of surface-stabilized polymer particles, described previously, of between 5% and 55% by weight, preferably between 5% and 50% by weight, more particularly from 8% to 45% by weight, preferably from 10% to 40% by weight and even more preferentially from 10% to 25% by weight relative to the weight of the composition (content expressed as active material).

Silicone Resin

The composition according to the invention comprises at least one silicone resin.

More generally, the term "resin" means a compound whose structure is three-dimensional. "Silicone resins" are also referred to as "siloxane resins". Thus, for the purposes of the present invention, a polydimethylsiloxane is not a silicone resin.

The nomenclature of silicone resins (also known as siloxane resins) is known under the name "MDTQ", the resin being described as a function of the various siloxane monomer units it comprises, each of the letters "MDTQ" characterizing a type of unit.

The letter M represents the monofunctional unit of formula R1R2R3SiO$_{1/2}$, the silicon atom being bonded to only one oxygen atom in the polymer comprising this unit.

The letter D means a difunctional unit R1R2SiO$_{2/2}$ in which the silicon atom is bonded to two oxygen atoms.

The letter T represents a trifunctional unit of formula R1SiO$_{3/2}$.

Such resins are described, for example, in the *Encyclopedia of Polymer Science and Engineering*, vol. 15, John Wiley & Sons, New York, (1989), pp. 265-270, and U.S. Pat. No. 2,676,182, U.S. Pat. No. 3,627,851, U.S. Pat. No. 3,772,247, U.S. Pat. No. 5,248,739 or U.S. Pat. No. 5,082,706, U.S. Pat. No. 5,319,040, U.S. Pat. No. 5,302,685 and U.S. Pat. No. 4,935,484.

In the units M, D and T defined previously, R, namely R1, R2 and R3, represents a hydrocarbon-based radical (especially alkyl) containing from 1 to 10 carbon atoms, a phenyl group, a phenylalkyl group or a hydroxyl group.

Finally, the letter Q means a tetrafunctional unit SiO$_{4/2}$ in which the silicon atom is bonded to four oxygen atoms, which are themselves bonded to the rest of the polymer.

Various silicone resins with different properties may be obtained from these different units, the properties of these polymers varying as a function of the type of monomer (or unit), the nature and number of the radical R, the length of the polymer chain, the degree of branching and the size of the pendent chains.

As silicone resins that may be used in the compositions according to the invention, use may be made, for example, of silicone resins of MQ type, of T type or of MQT type.

MQ Resins:

As examples of silicone resins of MQ type, mention may be made of the alkyl siloxysilicates of formula [(R1)$_3$SiO$_{1/2}$]$_x$(SiO$_{4/2}$)$_y$ (MQ units) in which x and y are integers ranging from 50 to 80, and such that the group R1 represents a radical as defined previously, and is preferably an alkyl group containing from 1 to 8 carbon atoms or a hydroxyl group, preferably a methyl group.

As examples of solid silicone resins of MQ type of trimethyl siloxysilicate type, mention may be made of those sold under the reference SR1000 by the company General Electric, under the reference TMS 803 by the company Wacker, or under the name KF-7312J by the company Shin-Etsu or DC749 or DC593 by the company Dow Corning.

As silicone resins comprising MQ siloxysilicate units, mention may also be made of phenylalkylsiloxysilicate resins, such as phenylpropyldimethylsiloxysilicate (Silshine 151 sold by the company General Electric). The preparation of such resins is described especially in U.S. Pat. No. 5,817,302.

T Resins:

Examples of silicone resins of type T that may be mentioned include the polysilsesquioxanes of formula (RSiO$_{3/2}$)$_x$ (units T) in which x is greater than 100 and such that the group R is an alkyl group containing from 1 to 10 carbon atoms, said polysilsesquioxanes also possibly comprising Si—OH end groups.

Polymethylsilsesquioxane resins that may preferably be used are those in which R represents a methyl group, for instance those sold:

by the company Wacker under the reference Resin MK, such as Belsil PMS MK: polymer comprising CH$_3$SiO$_{3/2}$ repeating units (units T), which may also comprise up to 1% by weight of (CH$_3$)$_2$SiO$_{2/2}$ units (units D) and having an average molecular weight of about 10 000 g/mol, or by the company Shin-Etsu under the reference KR220L, which are composed of units T of formula CH$_3$SiO$_{3/2}$ and have Si—OH (silanol) end groups, under the reference KR242A, which comprise 98% of units T and 2% of dimethyl units D and have Si—OH end groups, or alternatively under the reference KR251 comprising 88% of units T and 12% of dimethyl units D and have Si—OH end groups.

MQT Resins:

Resins comprising MQT units that are especially known are those mentioned in document U.S. Pat. No. 5,110,890.

A preferred form of resins of MQT type are MQT-propyl (also known as MQTpr) resins. Such resins that may be used in the compositions according to the invention are especially the resins described and prepared in patent application WO 2005/075 542.

The MQ-T-propyl resin preferably comprises the units:
(I) $(R1_3SiO_{1/2})_a$
(ii) $(R2_2SiO_{2/2})_b$
(iii) $(R3SiO_{3/2})_c$ and
(iv) $(SiO_{4/2})_d$
with
R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group,
a, b, c and d being mole fractions,
a being between 0.05 and 0.5,
b being between 0 and 0.3,
c being greater than zero,
d being between 0.05 and 0.6,
a+b+c+d=1,
on condition that more than 40 mol % of the groups R3 of the siloxane resin are propyl groups.

Preferably, the siloxane resin comprises the following units:
(I) $(R1_3SiO_{1/2})_a$
(iii) $(R3SiO_{3/2})_c$ and
(iv) $(SiO_{4/2})_d$
with
R1 and R3 independently representing an alkyl group containing from 1 to 8 carbon atoms, R1 preferably being a methyl group and R3 preferably being a propyl group,
a being between 0.05 and 0.5 and preferably between 0.15 and 0.4,
c being greater than zero, preferably between 0.15 and 0.4,
d being between 0.05 and 0.6, preferably between 0.2 and 0.6 or alternatively between 0.2 and 0.55,
a+b+c+d=1, and a, b, c and d being mole fractions,
on condition that more than 40 mol % of the groups R3 of the siloxane resin are propyl groups.

The siloxane resins that may be used according to the invention may be obtained via a process comprising the reaction of:
A) an MQ resin comprising at least 80 mol % of units $(R1_3SiO_{1/2})_a$ and $(SiO_{4/2})_d$,
R1 representing an alkyl group containing from 1 to 8 carbon atoms, an aryl group, a carbinol group or an amino group
a and d being greater than zero,
the ratio a/d being between 0.5 and 1.5,
and
B) a T-propyl resin comprising at least 80 mol % of units $(R3SiO_{3/2})_c$,
R3 representing an alkyl group containing from 1 to 8 carbon atoms, an aryl group, a carbinol group or an amino group,
c being greater than zero,
on condition that at least 40 mol % of the groups R3 are propyl groups,
in which the mass ratio NB is between 95/5 and 15/85 and preferably the mass ratio NB is 30/70.

Advantageously, the NB weight ratio is between 95/5 and 15/85. Preferably, the NB ratio is less than or equal to 70/30. These preferred ratios have proven to afford comfortable deposits.

Preferably, the composition according to the invention comprises, as silicone resin, at least one resin of MQ type as described previously.

According to a particular embodiment of the invention, the silicone resin is present in the composition in a resin solids content ranging from 2% to 20% by weight relative to the total weight of the composition, preferably ranging from 3% to 10% by weight relative to the weight of the composition.

Additional Silicone Oils

The composition according to the invention may also comprise at least one additional volatile or non-volatile, and preferably volatile, silicone oil.

The term "silicone oil" means an oil containing at least one silicon atom, and especially containing Si—O groups.

As additional volatile silicone oils that are suitable for use, examples that may be mentioned include volatile linear or cyclic silicone oils, especially those with a viscosity ≤8 centistokes ($8 \times 10^{-6}$ m$^2$/s) and especially containing from 2 to 7 silicon atoms, these silicones optionally comprising alkyl or alkoxy groups containing from 1 to 10 carbon atoms.

As volatile silicone oils that may be used, mention may be made especially of octamethylcyclotetrasiloxane, cyclopentadimethylsiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of non-phenyl non-volatile silicone oils, for instance polydimethylsiloxanes (PDMS), PDMSs comprising aliphatic groups, in particular alkyl or alkoxy, which are pendent and/or at the end of the silicone chain; these groups each comprising from 2 to 24 carbon atoms. An example that may be mentioned is cetyl dimethicone sold under the commercial reference Abil Wax 9801 from Evonik Goldschmidt.

Non-volatile phenyl silicone oils optionally comprising one or more dimethicone fragments (—(CH3)2-SiO—) are also suitable for use, for instance phenyl trimethicones, phenyl dimethicones, phenyltrimethylsiloxydiphenylsiloxanes, diphenyl dimethicones and trimethylpentaphenyltrisiloxane, and mixtures thereof.

If the composition comprises any, the content of additional, preferably volatile, oil(s) is between 1% and 15% by weight relative to the weight of the composition.

Preferably, the composition does not comprise more than 10% by weight and even more particularly not more than 5% by weight of additional non-volatile oil, relative to the weight of the composition, and preferably does not contain any.

Additional Film-Forming Agents

The composition may also comprise at least one additional film-forming polymer, other than the silicone resin and the polymer particles described previously.

Preferably, the additional film-forming agent(s) are chosen from hydrophobic polymers.

For the purposes of the invention, the term "polymer" means a compound corresponding to the repetition of one or more units (these units resulting from compounds known as monomers). This or these unit(s) are repeated at least twice and preferably at least three times.

The term "hydrophobic film-forming polymer" is intended to denote a film-forming polymer that has no affinity for water and, in this respect, does not lend itself to a formulation in the form of a solute in an aqueous medium. In particular, the term "hydrophobic polymer" means a polymer having a solubility in water at 25° C. of less than 1% by weight.

The term "film-forming polymer" means a polymer that is capable of forming, by itself or in the presence of an auxiliary film-forming agent, a macroscopically continuous deposit on a support, especially on keratin materials, and preferably a cohesive deposit, and better still a deposit whose cohesion and mechanical properties are such that said deposit can be isolable and manipulable in isolation, for example when said deposit is prepared by pouring onto a non-stick surface, such as a Teflon-coated or silicone-coated surface.

In particular, the hydrophobic film-forming polymer is a polymer chosen from the group comprising:

film-forming polymers that are soluble in an organic solvent medium, in particular liposoluble polymers; this means that the polymer is soluble or miscible in the organic medium and forms a single homogeneous phase when it is incorporated into the medium; and Hydrophobic film-forming polymers that may especially be mentioned include homopolymers and copolymers of a compound bearing an ethylenic unit, acrylic polymers and copolymers, polyurethanes, polyesters, silicone polymers, such as polymers bearing a non-silicone organic backbone grafted with monomers containing a polysiloxane, or polyisoprenes.

As hydrophobic film-forming polymers that are most particularly suitable for use in the invention, mention may be made especially of block ethylenic copolymers, vinyl polymers comprising at least one carbosiloxane dendrimer-based unit, and silicone acrylate copolymers, and mixtures thereof.

The content of additional film-forming polymer(s), if the composition comprises any, is less than or equal to 20% by weight, more particularly less than 15% by weight, preferably less than or equal to 10% by weight and even more preferentially less than or equal to 5% by weight, relative to the weight of the composition. The values are expressed as film-forming polymer active material.

Block Ethylenic Copolymer

The hydrophobic film-forming polymer may be a block ethylenic copolymer containing at least a first block with a glass transition temperature ($T_g$) of greater than or equal to 40° C. and being derived, totally or partly, from one or more first monomers which are such that the homopolymer prepared from these monomers has a glass transition temperature of greater than or equal to 40° C., and at least a second block with a glass transition temperature of less than or equal to 20° C. and being derived, totally or partly, from one or more second monomers which are such that the homopolymer prepared from these monomers has a glass transition temperature of less than or equal to 20° C., said first block and said second block being linked together via a random intermediate segment comprising at least one of said first constituent monomers of the first block and at least one of said second constituent monomers of the second block, and said block copolymer having a polydispersity index I of greater than 2.

Polymers of this type that are suitable for use in the invention are described in document EP 1 411 069.

As examples of such polymers, mention may be made more particularly of Mexomere PAS® (acrylic acid/isobutyl acrylate/isobornyl acrylate copolymer 50% diluted in isododecane) sold by the company Chimex.

Vinyl Polymer Comprising at Least One Carbosiloxane Dendrimer-Based Unit

The hydrophobic film-forming polymer may also be chosen from vinyl polymers comprising at least one carbosiloxane dendrimer-based unit.

The vinyl polymer(s) especially have a backbone and at least one side chain, which comprises a carbosiloxane dendrimer-based unit having a carbosiloxane dendrimer structure.

Vinyl polymers comprising at least one carbosiloxane dendrimer unit as described in patent applications WO 03/045 337 and EP 963 751 by the company Dow Corning may be used in particular.

In the context of the present invention, the term "carbosiloxane dendrimer structure" represents a molecular structure containing branched groups of high molecular masses, said structure having high regularity in the radial direction starting from the bond to the backbone. Such carbosiloxane dendrimer structures are described in the form of a highly branched siloxane-silylalkylene copolymer in laid-open Japanese patent application Kokai 9-171 154.

A vinyl polymer bearing at least one carbosiloxane dendrimer-based unit has a molecular side chain containing a carbosiloxane dendrimer structure, and may be derived from the polymerization of:

(A) from 0 to 99.9 parts by weight of a vinyl monomer; and (B) from 100 to 0.1 part by weight of a carbosiloxane dendrimer containing a radical-polymerizable organic group, represented by the general formula:

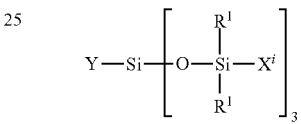

in which Y represents a radical-polymerizable organic group, $R^1$ represents an aryl group or an alkyl group containing from 1 to 10 carbon atoms, and $X^i$ represents a silylalkyl group which, when i=1, is represented by the formula:

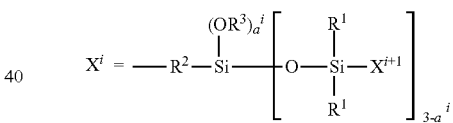

in which $R^1$ is as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group, or the silylalkyl group defined above with i=i+1; i is an integer from 1 to 10 which represents the generation of said silylalkyl group, and $a^i$ is an integer from 0 to 3;

in which said radical-polymerizable organic group contained in component (A) is chosen from:

organic groups containing a methacrylic group or an acrylic group and that are represented by the formulae:

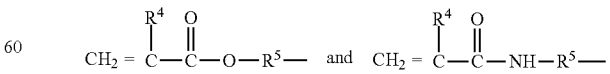

in which $R^4$ represents a hydrogen atom or an alkyl group, $R^5$ represents an alkylene group containing from 1 to 10 carbon atoms; and organic groups containing a styryl group and that are represented by the formula:

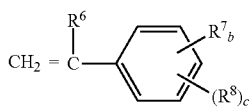

in which R$^6$ represents a hydrogen atom or an alkyl group, R$^7$ represents an alkyl group containing from 1 to 10 carbon atoms, R$^8$ represents an alkylene group containing from 1 to 10 carbon atoms, b is an integer from 0 to 4, and c is 0 or 1, such that if c is 0, —(R$^8$)$_c$— represents a bond.

The monomer of vinyl type that is component (A) in the vinyl polymer is a monomer of vinyl type that contains a radical-polymerizable vinyl group.

There is no particular limitation as regards such a monomer.

The following are examples of this monomer of vinyl type: methyl methacrylate, ethyl methacrylate, n-propyl methacrylate, isopropyl methacrylate or a methacrylate of an analogous lower alkyl; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or a higher-analogue methacrylate; vinyl acetate, vinyl propionate or a vinyl ester of an analogous lower fatty acid; vinyl caproate, vinyl 2-ethylhexoate, vinyl laurate, vinyl stearate or an ester of a higher fatty acid analogue; styrene, vinyltoluene, benzyl methacrylate, phenoxyethyl methacrylate, vinylpyrrolidone or similar vinylaromatic monomers; methacrylamide, N-methylolmethacrylamide, N-methoxymethylmethacrylamide, isobutoxymethoxymethacrylamide, N,N-dimethylmethacrylamide or similar monomers of vinyl type containing amide groups; hydroxyethyl methacrylate, hydroxypropyl alcohol methacrylate or similar monomers of vinyl type containing hydroxyl groups; acrylic acid, methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or a similar monomer of vinyl type with ether bonds; methacryloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional monomers of vinyl type may also be used.

The following are examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropane trioxyethylmethacrylate, tris(2-hydroxyethyl)isocyanurate dimethacrylate, tris(2-hydroxyethyl)isocyanurate trimethacrylate, polydimethylsiloxane capped with styryl groups possessing divinylbenzene groups on both ends, or analogous silicone compounds containing unsaturated groups.

To facilitate the preparation of a starting material mixture for cosmetic products, the number-average molecular mass of the vinyl polymer which contains a carbosiloxane dendrimer may be chosen within the range between 3000 g/mol and 2 000 000 g/mol and preferably between 5000 g/mol and 800 000 g/mol. It may be a liquid, a gum, a paste, a solid, a powder, or any other form. The preferred forms are solutions formed by dilution of a dispersion or of a powder in solvents such as a silicone oil or an organic oil.

A vinyl polymer contained in the dispersion or the solution may have a concentration within a range of between 0.1% and 95% by weight and preferably between 5% and 70% by weight. However, to facilitate the handling and the preparation of the mixture, the range should preferably be between 10% and 60% by weight.

According to a preferred mode, a vinyl polymer that is suitable for use in the invention may be one of the polymers described in the examples of patent application EP 0 963 751.

According to a preferred embodiment, a vinyl polymer grafted with a carbosiloxane dendrimer may be the product of polymerization of:

(A) from 0.1 to 99 parts by weight of one or more acrylate or methacrylate monomers; and (B) from 100 to 0.1 part by weight of an acrylate or methacrylate monomer of a tris[tri(trimethylsiloxy)silylethyldimethylsiloxy]silylpropyl carbosiloxane dendrimer.

According to one embodiment, a vinyl polymer bearing at least one carbosiloxane dendrimer-based unit may comprise a tris[tri(trimethylsiloxy)silylethyldimethylsiloxy]silylpropyl carbosiloxane dendrimer-based unit corresponding to one of the formulae:

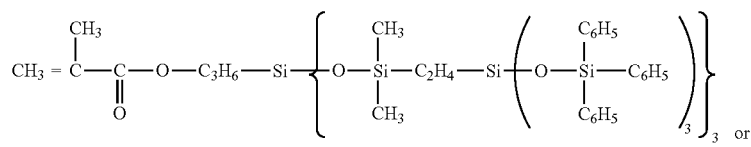

or

-continued

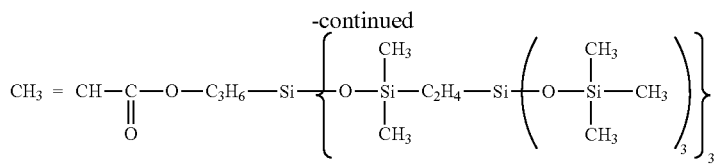

According to a preferred mode, a vinyl polymer bearing at least one carbosiloxane dendrimer-based unit used in the invention comprises at least one butyl acrylate monomer.

According to one embodiment, a vinyl polymer may also comprise at least one fluoro organic group. A fluorinated vinyl polymer may be one of the polymers described in the examples of patent application WO 03/045 337.

According to a preferred embodiment, a vinyl polymer grafted in the sense of the present invention may be conveyed in an oil or a mixture of oils, which are preferably volatile, chosen in particular from silicone oils and hydrocarbon-based oils, and mixtures thereof.

According to a particular embodiment, a silicone oil that is suitable for use in the invention may be cyclopentasiloxane.

According to another particular embodiment, a hydrocarbon-based oil that is suitable for use in the invention may be isododecane.

Vinyl polymers grafted with at least one carbosiloxane dendrimer-based unit that may be particularly suitable for use in the present invention are the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning. The polymers sold under the names FA 4002 ID (TIB 4-202) and FA 4001 CM (TIB 4-230) by the company Dow Corning will preferably be used.

Preferably, the vinyl polymer grafted with at least one carbosiloxane dendrimer-based unit that may be used in a composition of the invention is an acrylate/polytrimethyl siloxymethacrylate copolymer, especially the product sold in isododecane under the name Dow Corning FA 4002 ID Silicone Acrylate by the company Dow Corning.

Silicone Acrylate Copolymers

According to a particular embodiment, a composition used according to the invention may comprise, as hydrophobic film-forming polymer, at least one copolymer comprising carboxylate groups and polydimethylsiloxane groups.

In the present patent application, the term "copolymer comprising carboxylate groups and polydimethylsiloxane groups" means a copolymer obtained from (a) one or more carboxylic (acid or ester) monomers, and (b) one or more polydimethylsiloxane (PDMS) chains.

In the present patent application, the term "carboxylic monomer" means both carboxylic acid monomers and carboxylic acid ester monomers. Thus, the monomer (a) may be chosen, for example, from acrylic acid, methacrylic acid, maleic acid, fumaric acid, itaconic acid, crotonic acid, esters thereof and mixtures of these monomers. Esters that may be mentioned include the following monomers: acrylate, methacrylate, maleate, fumarate, itaconate and/or crotonate. According to a preferred embodiment of the invention, the monomers in ester form are more particularly chosen from linear or branched, preferably $C_1$-$C_{24}$ and better still $C_1$-$C_{22}$ alkyl acrylates and methacrylates, the alkyl radical preferably being chosen from methyl, ethyl, stearyl, butyl and 2-ethylhexyl radicals, and mixtures thereof.

Thus, according to a particular embodiment of the invention, the copolymer comprises as carboxylate groups at least one group chosen from acrylic acid and methacrylic acid, and methyl, ethyl, stearyl, butyl or 2-ethylhexyl acrylate or methacrylate, and mixtures thereof.

In the present patent application, the term "polydimethylsiloxanes" (also known as organopolysiloxanes and abbreviated as PDMS) is intended to denote, in accordance with what is generally accepted, any organosilicon polymer or oligomer of linear structure, of variable molecular weight, obtained by polymerization and/or polycondensation of suitably functionalized silanes, and formed essentially from a repetition of main units in which the silicon atoms are linked together via oxygen atoms (siloxane bond ≡Si—O—Si≡), comprising trimethyl radicals directly linked via a carbon atom to said silicon atoms. The PDMS chains that may be used to obtain the copolymer used according to the invention comprise at least one polymerizable radical group, preferably located on at least one of the ends of the chain, i.e. the PDMS may contain, for example, a polymerizable radical group on the two ends of the chain or one polymerizable radical group on one end of the chain and one trimethylsilyl end group on the other end of the chain. The polymerizable radical group may especially be an acrylic or methacrylic group, in particular a group $CH_2=CR_1$—COO—O—$R_2$, in which $R_1$ represents a hydrogen or a methyl group and $R_2$ represents —$CH_2$—, —$(CH_2)_n$— with n=3, 5, 8 or 10, —$CH_2$—$CH(CH_3)$—$CH_2$—, $CH_2$—$CH_2$—O—$CH_2$—$CH_2$—, —$CH_2$—$CH_2$—O—$CH_2$—$CH_2$—$CH(CH_3)$—$CH_2$—, —$CH_2$—$CH_2$—O—$CH_2CH_2$—O—$CH_2$—$CH_2$—.

The copolymers used in the composition of the invention are generally obtained according to the usual methods of polymerization and grafting, for example by free-radical polymerization (A) of a PDMS comprising at least one polymerizable radical group (for example on one of the ends of the chain or on both ends) and (B) of at least one carboxylic monomer, as described, for example, in documents U.S. Pat. No. 5,061,481 and U.S. Pat. No. 5,219,560.

The copolymers obtained generally have a molecular weight ranging from approximately 3000 g/mol to 200 000 g/mol and preferably from approximately 5000 g/mol to 100 000 g/mol.

The copolymer used in the composition of the invention may be in its native form or in dispersed form in a solvent such as lower alcohols containing from 2 to 8 carbon atoms, for instance isopropyl alcohol, or oils, for instance volatile silicone oils (for example cyclopentasiloxane).

As copolymers that may be used in the composition of the invention, mention may be made, for example, of copolymers of acrylic acid and of stearyl acrylate bearing polydimethylsiloxane grafts, copolymers of stearyl methacrylate bearing polydimethylsiloxane grafts, copolymers of acrylic acid and of stearyl methacrylate bearing polydimethylsiloxane grafts, copolymers of methyl methacrylate, butyl methacrylate, 2-ethylhexyl acrylate and stearyl methacrylate bearing polydimethylsiloxane grafts. As copolymers that may be used in the composition of the invention, mention may be made in particular of the copolymers sold by the company Shin-Etsu under the names KP-561 (CTFA name: acrylates/dimethicone), KP-541 in which the copolymer is dispersed at 60% by weight in isopropyl alcohol (CTFA name: acrylates/dimethicone and isopropyl alcohol), and KP-545 in which the copolymer is dispersed at 30% in cyclopentasiloxane (CTFA name: acrylates/dimethicone and cyclopentasiloxane). According to a preferred embodiment of the invention, KP561 is preferably used; this copolymer is not dispersed in a solvent, but is in waxy form, its melting point being about 30° C.

Mention may also be made of the grafted copolymer of polyacrylic acid and dimethylpolysiloxane dissolved in isododecane, sold by the company Shin-Etsu under the name KP-550.

Waxes

The composition according to the invention may optionally comprise at least one wax.

For the purposes of the present invention, the term "wax" means a lipophilic compound, which is solid at room temperature (25° C.), with a reversible solid/liquid change of state, which has a melting point of greater than or equal to 30° C. that may be up to 120° C.

The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes, and may be of plant, mineral, animal and/or synthetic origin. In particular, the waxes have a melting point of greater than 25° C. and better still greater than 45° C.

Hydrocarbon-based waxes, for instance beeswax, lanolin wax or Chinese insect wax; rice wax, carnauba wax, candelilla wax, ouricury wax, esparto grass wax, cork fibre wax, sugar cane wax, Japan wax and sumach wax; montan wax, microcrystalline waxes, paraffins and ozokerite; polyethylene waxes, the waxes obtained by Fisher-Tropsch synthesis and waxy copolymers, and also esters thereof, may especially be used.

Mention may also be made of waxes obtained by catalytic hydrogenation of animal or plant oils containing linear or branched $C_8$-$C_{32}$ fatty chains.

Among these waxes that may in particular be mentioned are hydrogenated jojoba oil, isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S by the company Heterene, bis(1,1,1-trimethylolpropane) tetrabehenate sold under the name Hest 2T-4B by the company Heterene.

Mention may also be made of silicone waxes, for instance alkyl or alkoxy dimethicones containing from 16 to 45 carbon atoms, polypropylsilsesquioxane waxes (as described in patent WO 2005/100444), in particular with the C30-C45 alkyldimethylsilyl polypropylsilsesquioxane compound commercially available from Dow Corning under the brand name SW-8005 C30 Resin Wax.

The wax obtained by hydrogenation of olive oil esterified with the stearyl alcohol, sold under the name Phytowax Olive 18 L 57 or else the waxes obtained by hydrogenation of castor oil esterified with cetyl alcohol, sold under the names Phytowax Castor 16L64 and 22L73 by the company Sophim, may also be used. Such waxes are described in patent application FR-A-2 792 190.

If the composition comprises any, the content of wax may represent from 0.1% to 30% by weight and advantageously from 0.3% to 20% by weight relative to the weight of the composition.

In accordance with a particular embodiment of the invention, the content of wax does not exceed 10% by weight relative to the weight of the composition, and even more particularly does not exceed 5% by weight, relative to the weight of the composition. According to certain embodiments of the invention, the composition is free of wax.

Dyestuffs

The compositions in accordance with the invention may comprise at least one dyestuff.

This (or these) dyestuff(s) are preferably chosen from pulverulent substances, liposoluble dyes and water-soluble dyes, and mixtures thereof.

Preferably, the compositions according to the invention comprise at least one pulverulent dyestuff. The pulverulent dyestuffs may be chosen from pigments and nacres, and preferably from pigments.

The pigments may be white or coloured, mineral and/or organic, and coated or uncoated. Among the mineral pigments, mention may be made of metal oxides, in particular titanium dioxide, optionally surface-treated, zirconium, zinc or cerium oxide, and also iron, titanium or chromium oxide, manganese violet, ultramarine blue, chromium hydrate and ferric blue. Among the organic pigments that may be mentioned are carbon black, pigments of D&C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the pigments contained in the compositions according to the invention are chosen from metal oxides. More preferentially, the pigments contained in the compositions according to the invention are chosen from iron oxides, such as especially those sold under the name Sunpuro Black Iron Oxide C33-7001® by the company Sun.

These dyestuffs may be present in a content ranging from 2% to 15% by weight relative to the total weight of the composition and in particular from 4% to 10% by weight relative to the total weight of the composition.

Fibres

The composition according to the invention may also comprise at least one fibre.

The term "fibre" should be understood as meaning an object of length L and of diameter D such that L is greater than D and preferably very much greater than D, D being the diameter of the circle in which the cross section of the fibre is inscribed. In particular, the ratio L/D (or aspect ratio) is chosen in the range from 3.5 to 2,500, preferably from 5 to 500 and better still from 5 to 150.

The fibres that may be used in the composition of the invention may be mineral or organic fibres, of synthetic or natural origin. They may be short or long, individual or organized, for example braided, and hollow or solid. They may have any shape and may especially have a circular or polygonal (square, hexagonal or octagonal) cross section depending on the specific application envisaged. In particular, their ends are blunted and/or polished to prevent injury.

In particular, the fibres have a length ranging from 1 µm to 10 mm, preferably from 0.1 mm to 5 mm and better still from 0.3 mm to 3 mm. They may have a cross section included within a circle with a diameter ranging from 2 nm to 500 µm, preferably ranging from 100 nm to 100 µm and better still from 1 µm to 50 µm. The weight or yarn count of fibres is often given in denier or decitex and represents the weight in grams per 9 km of yarn. Preferably, the fibres according to the invention have a yarn count chosen in the range from 0.01 to 10 denier, preferably from 0.1 to 2 denier and better still from 0.3 to 0.7 denier.

The fibres that may be used in the compositions according to the invention may be chosen from rigid or non-rigid fibres, and may be of synthetic or natural, mineral or organic origin.

Moreover, the fibres may or may not be surface-treated, may be coated or uncoated, and may be coloured or uncoloured.

As fibres that may be used in the compositions according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours.

The fibres may be present in a content of less than or equal to 10% by weight and preferably less than or equal to 5% by weight, relative to the weight of the composition.

Additional Fillers

The term "fillers" should be understood as meaning colourless or white solid particles of any form, which are in a form that is insoluble and dispersed in the medium of the composition, and are of mineral or organic nature.

In the present patent application, "mineral filler" is understood to mean any mineral solid that is insoluble in the medium at room temperature (25° C.).

The term "mineral" refers to any compound or polymer whose chemical structure does not comprise any carbon atoms.

The fillers may or may not be surface-coated, and in particular they may be surface-treated with silicones, amino acids, fluoro derivatives or any other substance that promotes the dispersion and compatibility of the filler in the composition.

Such fillers are distinct from the mineral thickeners and also from the colouring agents described previously.

The fillers may be spherical, i.e. they may comprise at least a rounded general portion, preferably defining at least a sphere portion, preferably internally defining a concavity or a hollow (sphere, globules, bowls, horseshoe, and the like), or lamellar.

Such fillers are advantageously chosen from:
  silica powders, such as the porous silica microspheres sold under the name Silica Beads SB-700 by the company Miyoshi or Sunsphere® H51 or Sunsphere® H33 by the company Asahi Glass; or the polydimethylsiloxane-coated amorphous silica microspheres sold under the name SA Sunsphere® H33 or SA Sunsphere® H53 by the company Asahi Glass,
  acrylic (co)polymer powders and derivatives thereof, in particular:
    the polymethyl methacrylate powder sold under the names Covabead® LH85 by the company Wackherr or Microsphere-M100® by the company Matsumoto,
    the polymethyl methacrylate/ethylene glycol dimethacrylate powder sold under the name Dow Corning 5640 Microsponge® Skin Oil Adsorber by the company Dow Corning or Ganzpearl® GMP-0820 by the company Ganz Chemical,
    the polyallyl methacrylate/ethylene glycol dimethacrylate powder sold under the name Poly-Pore® L200 or Poly-Pore® E200 by the company Amcol Health and Beauty Solutions Inc.,
    the ethylene glycol dimethacrylate/lauryl methacrylate copolymer powder sold under the name Polytrap® 6603 by the company Dow Corning,
    optionally crosslinked acrylate/alkyl acrylate copolymer powder crosslinked acrylate/ethylhexyl acrylate copolymer powder sold under the name Techpolymer ACP-8C by the company Sekisui Plastics,
    ethylene/acrylate copolymer powder, such as the product sold under the name Flobeads® by the company Sumitomo Seika Chemicals,
    the expanded hollow particles of acrylonitrile (co) polymer sold under the name Expancel by Expancel or the microspheres sold under the name Micropearl F 80 ED® by the company Matsumoto,
  the polyurethane powders sold, for example, under the names Plastic Powder D-400, Plastic Powder CS-400, Plastic Powder D-800 and Plastic Powder T-75 by the company Toshiki,
  silicone powders advantageously chosen from:
    polymethylsilsesquioxane powders, in particular those sold under the name Tospearl, in particular Tospearl 145 A, by the company Momentive Performance Materials,
    organopolysiloxane elastomer powders coated with silicone resin, especially with silsesquioxane resin, such as the products sold under the name KSP-100, KSP-101, KSP-102, KSP-103, KSP-104 or KSP-105 by the company Shin-Etsu (INCI name: vinyl dimethicone/methicone silsesquioxane crosspolymer),
    silicone elastomer powders, such as the products sold under the name Trefil® Powder E-505C or Trefil® Powder E-506C by the company Dow Corning,
    powders of organosilicone particles, for example, in the form of bowls, such as those described in JP-2003 128 788 or JP-A-2000-191789 or also in patent application EP 1 579 841 and sold especially by the company Takemoto Oil & Fat,
  polyamide powders, such as Nylon® powders, in particular Nylon 12 powders, such as the nylon powders sold under the name Orgasol® 2002 EXS NAT COS by the company Arkema,
  powders of natural organic materials, such as polysaccharide powders and in particular starch powders, especially crosslinked or non-crosslinked corn, wheat or rice starch powders, powders of starch crosslinked with octenylsuccinic anhydride sold under the name Dry-Flo® by the company National Starch or powders of waxy corn starch, such as those which are sold under the names C* Gel 04201 by the company Cargill, Corn Starch B by the company Roquette and Organic Corn Starch by the company Draco Natural Products,
  spherical cellulose microparticles, such as Cellulobeads D-10, Cellulobeads D-5 and Cellulobeads USF, sold by the company Daito Kasei Kogyo, particles of N—($C_8$-$C_{22}$ carbon atoms acylated) amino acids; the amino acid may be, for example, lysine, glutamic acid or alanine, preferably lysine, for example Amihope LL by the company Ajinomoto or the product sold under the name Corum 5105 S by the company Corum, Perlite powders, such as those sold by the company World Minerals under the trade name Perlite P1430, Perlite P2550, Perlite P2040 or OpTiMat™ 1430 OR or 2550 OR. Europerl EMP-2 and Europerl 1 by the company Imerys, zeolites, such as the products sold by the company Zeochem under the names Zeoflair 300, Zeoflair 200, Zeoflair 100, X-Mol and X-Mol MT, calcium magnesium carbonate particles, such as those sold by the company Imerys under the name Calcidol, by LCW (Sensient) under the name Carbomat or by the company Omya under the name Omyacare 60-AV.

Use may also be made of talc particles, for example sold under the names Luzenac Pharma M and UM by the company Imerys and Rose Talc and Talc SG-2000 by the company Nippon Talc; natural or synthetic mica particles, such as those sold under the names Mica M RP and Silk Mica by the company Merck, or the product sold under the name Sericite S-152-BC by the company Miyoshi Kasei; calcium carbonate and magnesium hydrogen carbonate; hydroxyapatite; boron nitride; fluorphlogopite; and mixtures thereof.

The spherical fillers may be coated with a hydrophobic treatment agent. The hydrophobic treatment agent may be chosen from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate, and mixtures thereof. The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine. The term "alkyl" mentioned in the compounds cited above especially denotes an alkyl group containing from 1 to 30 carbon atoms and preferably containing from 5 to 16 carbon atoms.

The composition advantageously has a content of additional filler(s) of less than or equal to 10% by weight and preferably less than or equal to 5% by weight, relative to the weight of the composition. Preferably, the composition is free of fillers.

Optional Additives

The composition may comprise at least one optional ingredient chosen, for example, from antioxidants; preserving agents; fragrances; flavourings; neutralizers; emollients; plasticizers; moisturizers; vitamins, and mixtures thereof.

According to one embodiment of the invention, the composition comprises at least one plasticizer. In the case where the polymer particles are provided in the form of a dispersion, the plasticizer is then advantageously present in said oily dispersion.

The plasticizer(s) may be chosen from tri-n-butyl citrate, tripropylene glycol monomethyl ether (INCI name: PPG-3 methyl ether) and trimethyl pentaphenyl trisiloxane (sold under the name Dow Corning PH-1555 HRI Cosmetic Fluid by the company Dow Corning). These plasticizers make it possible to improve the mechanical strength of the polymer film.

The plasticizer may be present in an amount ranging from 5% to 50% by weight, relative to the total weight of the polymer of the particles, or relative to the total weight of the composition.

Needless to say, a person skilled in the art will take care to select the optional additional additives and/or the amount thereof such that the advantageous properties of the composition according to the invention are not, or are not substantially, adversely affected by the envisaged addition.

The compositions according to the invention are thus intended for caring for and/or making up keratin materials, in particular the skin or the lips, and also keratin fibres especially such as the eyelashes or the eyebrows.

They advantageously contain a physiologically acceptable medium, in other words a medium that is compatible with the treated keratin materials.

The compositions according to the invention may be in fluid or solid form. Preferably, the compositions are in fluid form.

The term "fluid" refers to compositions for which it is possible to measure the viscosity at 25° C. and atmospheric pressure ($1.013 \times 10^5$ Pa).

The compositions according to the invention may also be in anhydrous form, or in the form of oil-in-water or water-in-oil emulsions.

If the compositions comprise water, the water content advantageously does not exceed 15% by weight and even more particularly does not exceed 10% by weight relative to the weight of the composition. Preferably, if it is present, the water content does not exceed 5% by weight relative to the weight of the composition.

In accordance with a preferred embodiment of the invention, the compositions are anhydrous.

The term "anhydrous" means that water is not deliberately added to the compositions, but may be present in trace amount in the various compounds used in the compositions.

Advantageously, the composition according to the invention is a makeup composition, in particular compositions of mascara or eyeliner type.

Preferably, the hydrocarbon-based oil present in the composition is chosen from volatile, preferably apolar, oils.

Furthermore, these compositions are advantageously pigmented. Reference may be made to the description as regards the nature and content of these compounds.

As regards mascaras and eyeliners, these compositions conventionally have a viscosity at 25° C. and atmospheric pressure ($1.013 \times 10^5$ Pa) of from 0.1 to 50 Pa·s and in particular from 1 to 30 Pa·s.

In the case of mascaras, the viscosity is more particularly greater than or equal to 4 Pa·s (measured with a Rheomat RM100® machine).

Advantageously, if these compositions comprise at least one non-volatile oil, the content of this/these non-volatile oil(s) remains less than 5% by weight relative to the weight of the composition. In accordance with an even more preferred embodiment, these compositions are free of non-volatile oil(s).

According to one variant of the invention, besides the polymer particles, preferably incorporated in the form of a dispersion in a hydrocarbon-based oil, which is preferably volatile, and the silicone resin, such compositions comprise at least one additional film-forming agent.

The additional film-forming agent(s) are preferably present in a content of less than 20% by weight and preferably less than 10% by weight relative to the weight of the composition.

Advantageously, according to this variant, the content of non-volatile oil is less than 5% by weight relative to the weight of the composition. In accordance with an even more preferred embodiment, the composition is free of non-volatile oil.

According to a particular embodiment of this variant, the composition comprises a content of additional filler(s) of less than 5% by weight, more particularly less than 2% by weight and even more preferentially less than 1% by weight, relative to the weight of the composition. Even more particularly, the composition according to this variant is free of said filler(s).

The invention is illustrated in more detail in the following examples.

All the percentages of reagents described in the examples are weight percentages.

SYNTHESIS EXAMPLES

Example 1

In a first step, 1300 g of isododecane, 337 g of isobornyl acrylate, 28 g of methyl acrylate and 3.64 g of tert-butyl peroxy-2-ethylhexanoate (Trigonox 21S from Akzo) were placed in a reactor. The isobornyl acrylate/methyl acrylate mass ratio is 92/8. The mixture was heated at 90° C. under argon with stirring.

After 2 hours of reaction, 1430 g of isododecane were added to the reactor feedstock and the mixture was heated to 90° C.

In a second step, a mixture of 1376 g of methyl acrylate, 1376 g of isododecane and 13.75 g of Trigonox 21S were run in over 2 hours 30 minutes, and the mixture was left to react for 7 hours. 3.3 liters of isododecane were then added and part of the isododecane was evaporated off to obtain a solids content of 50% by weight.

A dispersion of methyl acrylate particles stabilized with a statistical copolymer stabilizer containing 92% isobornyl acrylate and 8% methyl acrylate in isododecane was obtained.

The oily dispersion contains in total (stabilizer+particles) 80% methyl acrylate and 20% isobornyl acrylate.

The polymer particles of the dispersion have a number-average size of about 160 nm.

The dispersion is stable after storage for 7 days at room temperature (25° C.).

Example 2

A dispersion of polymer in isododecane was prepared according to the preparation method of Example 1, using:

Step 1: 275.5 g of isobornyl acrylate, 11.6 g of methyl acrylate, 11.6 g of ethyl acrylate, 2.99 g of Trigonox 21, 750 g of isododecane; followed by addition, after reaction, of 750 g of isododecane.

Step 2: 539.5 g of methyl acrylate, 539.5 g of ethyl acrylate, 10.8 g of Trigonox 21S, 1079 g of isododecane. After reaction, addition of 2 liters of isododecane and evaporation to obtain a solids content of 35% by weight.

A dispersion in isododecane of methyl acrylate/ethyl acrylate (50/50) copolymer particles stabilized with an isobornyl acrylate/methyl acrylate/ethyl acrylate (92/4/4) statistical copolymer stabilizer was obtained.

The oily dispersion contains in total (stabilizer+particles) 40% methyl acrylate, 40% ethyl acrylate and 20% isobornyl acrylate.

The dispersion is stable after storage for 7 days at room temperature (25° C.).

Example 3

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 303 g of methyl acrylate, 776 g of ethyl acrylate, 157 g of acrylic acid, 11 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (24.5/62.8/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 20% methyl acrylate, 50% ethyl acrylate and 20% isobornyl acrylate.

The dispersion is stable after storage for 7 days at room temperature (25° C.).

Example 4

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 145 g of methyl acrylate, 934 g of ethyl acrylate, 157 g of acrylic acid, 12.36 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (11.7/75.6/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 10% methyl acrylate, 60% ethyl acrylate and 20% isobornyl acrylate.

The dispersion is stable after storage for 7 days at room temperature (25° C.).

Example 5

A dispersion of polymer in isododecane was prepared according to the preparation method of Example 1, using:

Step 1: 48 g of isobornyl acrylate, 2 g of methyl acrylate, 2 g of ethyl acrylate, 0.52 g of Trigonox 21, 57.6 g of isododecane, 38.4 g of ethyl acetate; followed by addition, after reaction, of 540 g of isododecane and 360 g of ethyl acetate.

Step 2: 98 g of methyl acrylate, 73 g of ethyl acrylate, 25 g of maleic anhydride, 1.96 g of Trigonox 21S, 50.4 g of isododecane and 33.60 g of ethyl acetate. After reaction, addition of 1 liter of an isododecane/ethyl acetate mixture (60/40 weight/weight) and total evaporation of the ethyl acetate and partial evaporation of the isododecane to obtain a solids content of 46.2% by weight.

A dispersion in isododecane of methyl acrylate/ethyl acrylate/maleic anhydride (50/37.2/12.8) copolymer particles stabilized with an isobornyl acrylate/methyl acrylate/ethyl acrylate (92/4/4) statistical copolymer stabilizer was obtained.

The oily dispersion contains in total (stabilizer+particles) 10% maleic anhydride, 30% methyl acrylate, 40% ethyl acrylate and 20% isobornyl acrylate.

The dispersion is stable after storage for 7 days at room temperature (25° C.).

Example 6

A dispersion of polymer in isododecane was prepared according to the preparation method of Example 1, using:

Step 1: 48.5 g of isobornyl methacrylate, 4 g of methyl acrylate, 0.52 g of Trigonox 21, 115 g of isododecane; followed by addition, after reaction, of 80 g of isododecane.

Step 2: 190 g of methyl acrylate, 1.9 g of Trigonox 21S, 190 g of isododecane. After reaction, addition of 1 liter of isododecane and partial evaporation of the isododecane to obtain a solids content of 48% by weight.

A dispersion in isododecane of methyl acrylate polymer particles stabilized with an isobornyl methacrylate/methyl acrylate (92/8) statistical copolymer stabilizer was obtained.

The oily dispersion contains in total (stabilizer+particles) 80% methyl acrylate and 20% isobornyl methacrylate.

The dispersion is stable after storage for 7 days at room temperature (25° C.).

Example 7

Eyeliner

The following compositions, the ingredients of which are collated in the table below, are prepared. Compositions 1 and 2 are in accordance with the invention; composition A is a comparative composition.

The amounts are indicated as weight of starting materials.

| Ingredients | 1 | 2 | A |
|---|---|---|---|
| (Methyl acrylate)-co-(isobornyl acrylate) copolymer in isododecane (according to Example 1) | 38.7 | 90 | — |
| Acrylic acid/isobutyl acrylate/isobornyl acrylate copolymer (Mexomere PAS from Chimex) | 38.7 | — | — |
| Trimethyl siloxysilicate (SR1000 from Momentive Performance Materials) | 6.75 | 10 | — |
| Mica (Sericite S-152-BC from Miyoshi Kasei) | — | — | 10 |
| Iron oxides (Sunpuro C33-7001, Sun) | 10 | — | — |
| Preserving agent | 2.7 | — | — |

Protocol for Preparing Said Compositions

The starting materials, weighed out beforehand, are heated using a jacketed heating pan (90° C.).

The mixture is stirred for 45 minutes using a Rayneri blender until a smooth and homogeneous preparation is obtained.

The preparation is cooled to room temperature.

The composition thus obtained is transferred into a closed container to prevent it from drying out on contact with air.

After 24 hours, the satisfactory nature of the homogeneity and dispersion of the pigment are evaluated.

Evaluation of the Gloss:

The composition is evaluated on a contrast card (for example Byko-charts from the company Byk-Gardner) by depositing a film of 150 μm which has dried for 24 hours at room temperature (25° C.).

The gloss of the film was measured using a Byk Spectro-guide 45/0 gloss glossmeter at 60°.

Results:

Compositions 1 and 2 according to the invention have a gloss value of 61.6 and 71.9, respectively, whereas the comparative composition has a gloss value of only 34.8.

The compositions according to the invention are thus significantly more glossy than the comparative composition.

Examples 8 and 9 (Invention) and 10 and 11 (Outside the Invention)

Several oily dispersions of polymethyl acrylate stabilized with a stabilizer containing isobornyl acrylate and optionally methyl acrylate were prepared, according to the procedure of Example 1, by varying the mass ratio of isobornyl acrylate and methyl acrylate and observing the stability of the dispersion obtained as a function of the chemical constitution of the stabilizer.

All the dispersions comprise in total (stabilizer+particles) 80% methyl acrylate and 20% isobornyl acrylate.

Example 8

Step 1: 50 g of isobornyl acrylate, 0.5 g of Trigonox 21, 96 g of isododecane; followed by addition, after reaction, of 80 g of isododecane.

Step 2: 200 g of methyl acrylate, 2 g of Trigonox 21S, 200 g of isododecane. After reaction, addition of 80 g of isododecane and evaporation to obtain a solids content of 31% by weight.

A dispersion in isododecane of polymethyl acrylate particles stabilized with a poly-isobornyl acrylate stabilizer was obtained.

Example 9

Step 1: 48.5 g of isobornyl acrylate, 8.5 g of methyl acrylate, 0.57 g of Trigonox 21, 115 g of isododecane; followed by addition, after reaction, of 75 g of isododecane.

Step 2: 185.5 g of methyl acrylate, 1.85 g of Trigonox 21S, 185.5 g of isododecane. After reaction, addition of 75 g of isododecane and evaporation to obtain a solids content of 31% by weight.

A dispersion in isododecane of polymethyl acrylate particles stabilized with an isobornyl acrylate/methyl acrylate (85/15) statistical copolymer stabilizer was obtained.

Example 10

Outside the Invention

Step 1: 48.5 g of isobornyl acrylate, 12 g of methyl acrylate, 0.6 g of Trigonox 21, 115 g of isododecane; followed by addition, after reaction, of 60 g of isododecane.

Step 2: 182 g of methyl acrylate, 1.82 g of Trigonox 21S, 182 g of isododecane. After reaction, addition of 60 g of isododecane and evaporation to obtain a solids content of 31% by weight.

A dispersion in isododecane of polymethyl acrylate particles stabilized with an isobornyl acrylate/methyl acrylate (80/20) statistical copolymer stabilizer was obtained.

Example 11

Outside the Invention

Step 1: 48.5 g of isobornyl acrylate, 21 g of methyl acrylate, 0.7 g of Trigonox 21, 130 g of isododecane; followed by addition, after reaction, of 65 g of isododecane.

Step 2: 173 g of methyl acrylate, 1.73 g of Trigonox 21S, 173 g of isododecane. After reaction, addition of 65 g of isododecane and evaporation to obtain a solids content of 31% by weight.

A dispersion in isododecane of polymethyl acrylate particles stabilized with an isobornyl acrylate/methyl acrylate (70/30) statistical copolymer stabilizer was obtained.

The stability 12 hours after the end of synthesis of the oily dispersions of polymethyl acrylate of Examples 1 and 8 to 11 was compared, and the following results were obtained.

| Example | Stabilizer | Stability |
| --- | --- | --- |
| 1 | 92 isobornyl acrylate/8 methyl acrylate | stable |
| 8 | 100 isobornyl acrylate | stable |
| 9 | 85 isobornyl acrylate/15 methyl acrylate | stable |
| 10 | 80 isobornyl acrylate/20 methyl acrylate | Phase separation and setting to a solid |
| 11 | 70 isobornyl acrylate/30 methyl acrylate | Phase separation and setting to a solid |

The results obtained show that the dispersions of polymethyl acrylate in isododecane are stable when the stabilizer is an isobornyl acrylate homopolymer or an isobornyl acrylate/methyl acrylate copolymer with an isobornyl acrylate/methyl acrylate weight ratio >80/20.

Moreover, the film obtained with the oily dispersions of Examples 1, 7 and 8 have the following properties:

| Gloss at 20° | Resistance to fatty substances | Tacky |
| --- | --- | --- |
| 72 | Resistant to fatty substances | Non-tacky |
| 69 | Resistant to fatty substances | Non-tacky |
| 65 | Resistant to fatty substances | Non-tacky |

Examples 12 and 13

Outside the Invention

Tests were performed with other monomers bearing a cyclic group by replacing the isobornyl acrylate, performing step 1 of Example 1, i.e. preparing a cyclic monomer/methyl acrylate (92/8) statistical copolymer stabilizer. All the stabilizers prepared in isododecane led to a medium that set to a solid in the form of a viscous precipitate. This shows that such stabilizers are unsuitable for forming an oily dispersion since they are incompatible with isododecane, in contrast with the stabilizers prepared in Examples 1 to 9 described previously.

| Examples | Stabilizer | Compatibility in isododecane |
| --- | --- | --- |
| 12 | Cyclohexyl acrylate/methyl acrylate (92/8) | Incompatible (viscous precipitate) |
| 13 | Cyclohexyl methacrylate/methyl acrylate (92/8) | Incompatible (viscous precipitate) |

The invention claimed is:

1. A composition comprising:
   particles of at least one polymer that is surface-stabilized with a stabilizer, the polymer of the particles being a $C_1$-$C_4$ alkyl (meth)acrylate polymer; the stabilizer being an isobornyl (meth)acrylate polymer selected from the group consisting of an isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4;
   at least one hydrocarbon-based oil; and
   at least one silicone resin.

2. The composition according to claim 1, wherein the polymer of the particles is a methyl acrylate and/or ethyl acrylate polymer.

3. The composition according to claim 1, wherein the polymer of the particles comprises an ethylenically unsaturated acid monomer or the anhydride thereof selected from the group consisting of (meth)acrylic acid, maleic acid and maleic anhydride.

4. The composition according to claim 1, wherein the polymer of the particles is selected from the group consisting of:
   methyl acrylate homopolymers,
   ethyl acrylate homopolymers,
   methyl acrylate/ethyl acrylate copolymers,
   methyl acrylate/ethyl acrylate/acrylic acid copolymers,
   methyl acrylate/ethyl acrylate/maleic anhydride copolymers,
   methyl acrylate/acrylic acid copolymers,
   ethyl acrylate/acrylic acid copolymers,
   methyl acrylate/maleic anhydride copolymers, and
   ethyl acrylate/maleic anhydride copolymers.

5. The composition according to claim 1, wherein the stabilizer is a statistical copolymer of isobornyl (meth)acrylate and of C1-C4 alkyl (meth)acrylate and an isobornyl (meth)acrylate/C1-C4 alkyl (meth)acrylate weight ratio is greater than or equal to 5.

6. The composition according to claim 1, wherein the stabilizer is selected from the group consisting of:
   isobornyl acrylate homopolymers,
   statistical copolymers of isobornyl acrylate/methyl acrylate,
   statistical copolymers of isobornyl acrylate/methyl acrylate/ethyl acrylate, and
   statistical copolymers of isobornyl methacrylate/methyl acrylate.

7. The composition according to claim 1, wherein the hydrocarbon-based oil is selected from the group consisting of apolar hydrocarbon-based oils containing from 8 to 16 carbon atoms.

8. The composition according to claim 1, wherein the content of hydrocarbon-based oil ranges from 20% to 75% by weight relative to the weight of the composition.

9. The composition according to claim 1, wherein the content of polymer particles ranges from 5% to 55% by weight, expressed as polymer particle solids, relative to the weight of the composition.

10. The composition according to claim 1, wherein the silicone resins are silicone resins of MQ type, selected from the group consisting of (i) alkyl siloxy silicates of formula $$[(R_1)_3SiO_{1/2}]_x(SiO_{4/2})_y,$$

wherein x and y are integers ranging from 50 to 80, and such that the group $R_1$ represents a hydrocarbon-based radical containing from 1 to 10 carbon atoms, a phenyl group, a phenylalkyl group or a hydroxyl group, and (ii) phenylalkyl siloxysilicate resins.

11. The composition according to claim 1, wherein the silicone resins are silicone resins of T type, selected from the group consisting of polysilsesquioxanes of formula $$(RSiO_{3/2})_x$$

wherein x is greater than 100 and the group R is an alkyl group containing from 1 to 10 carbon atoms, optionally comprising Si—OH end groups.

12. The composition according to claim 1, wherein the silicone resins are silicone resins of MQT-propyl type, which may comprise the following units:
(i) $((R_1)_3SiO_{1/2})_a$,
(ii) $((R_2)_2SiO_{2/2})_b$,
(iii) $(R_3SiO_{3/2})_c$ and
(iv) $(SiO_{4/2})_d$
wherein $R_1$, $R_2$ and $R_3$ are each independently a alkyl group, containing from 1 to 10 carbon atoms, a phenyl group, a phenylalkyl group or a hydroxyl group,
a being between 0.05 and 0.5,
b being between 0 and 0.3,
c being greater than zero,
d being between 0.05 and 0.6,
a+b+c+d=1, and a, b, c and d being mole fractions,
with the proviso that more than 40 mol % of the groups R3 of the siloxane resin are propyl groups.

13. The composition according to claim 12, wherein the silicone resins are selected from silicone resins comprising units (i) $((R_1)_3SiO_{1/2})_a$, (iii) $(R_3SiO_{3/2})_c$ and (iv) $(SiO_{4/2})_d$ with
$R_1$ and $R_3$ independently representing an alkyl group containing from 1 to 8 carbon atoms,
a being between 0.05 and 0.5,
c being between 0.15 and 0.4,
d being between 0.05 and 0.6,
a+b+c+d=1, and a, b, c and d being mole fractions,
with the proviso that more than 40 mol % of the groups R3 of the siloxane resin are propyl groups.

14. The composition according to claim 1, wherein the content of silicone resin(s) represents from 2% to 20% by weight relative to the weight of the composition.

15. The composition according to claim 1, wherein the polymer particles surface-stabilized with a stabilizer are incorporated into the composition in the form of a dispersion in at least one hydrocarbon-based oil.

16. The composition according to claim 1, further comprising: at least one additional film-forming polymer other than the silicone resin and the polymer particles.

17. The composition according to claim 16, wherein the further comprised film-forming polymer is selected from homopolymers and copolymers of compounds bearing an ethylenic unit, acrylic polymers and copolymers, polyurethanes, polyesters, silicone polymers bearing a non-silicone organic backbone grafted with monomers containing a polysiloxane, polyisoprenes, and also mixtures thereof.

18. The composition according to claim 16, wherein the content of the further comprised film-forming polymer is less than or equal to 15% by weight relative to the weight of the composition.

19. A process for making up and/or caring for human keratin materials, comprising applying the composition according to claim 1 to the keratin material.

* * * * *

UNITED STATES PATENT AND TRADEMARK OFFICE
CERTIFICATE OF CORRECTION

| | | |
|---|---|---|
| PATENT NO. | : 10,219,991 B2 | Page 1 of 1 |
| APPLICATION NO. | : 15/537082 | |
| DATED | : March 5, 2019 | |
| INVENTOR(S) | : Laure Daubersies et al. | |

It is certified that error appears in the above-identified patent and that said Letters Patent is hereby corrected as shown below:

In the Claims

In Column 29, Line 7, Claim 10, delete "siloxy silicates" and insert -- siloxysilicates --, therefor.

In Column 28, Line 48 and 49, Claim 5, delete "C1-C4" and insert -- $C_1$-$C_4$ --.

In Column 29, Line 38, Claim 12, delete "R3" and insert -- $R_3$ --.

In Column 30, Line 12, Claim 13, delete "R3" and insert -- $R_3$ --.

Signed and Sealed this
Twenty-eighth Day of April, 2020

Andrei Iancu
*Director of the United States Patent and Trademark Office*